United States Patent
Crabtree

(10) Patent No.: US 9,474,825 B2
(45) Date of Patent: Oct. 25, 2016

(54) METHODS FOR SEALING FLUID LEAKS IN LUNG TISSUE

(76) Inventor: Traves Dean Crabtree, Glen Carbon, IL (US)

( * ) Notice: Subject to any disclaimer, the term of this patent is extended or adjusted under 35 U.S.C. 154(b) by 1808 days.

(21) Appl. No.: 11/945,060

(22) Filed: Nov. 26, 2007

(65) Prior Publication Data

US 2009/0136589 A1  May 28, 2009

(51) Int. Cl.
*A61L 24/02* (2006.01)

(52) U.S. Cl.
CPC .................................... *A61L 24/02* (2013.01)

(58) Field of Classification Search
None
See application file for complete search history.

(56) References Cited

U.S. PATENT DOCUMENTS

| | | | |
|---|---|---|---|
| 5,552,452 A | 9/1996 | Khadem et al. | |
| 5,660,857 A | 8/1997 | Haynes et al. | |
| 6,001,895 A | 12/1999 | Harvey et al. | |
| 6,015,844 A | 1/2000 | Harvey et al. | |
| 6,183,498 B1 | 2/2001 | Devore et al. | |
| 6,518,212 B1 * | 2/2003 | Wagh et al. | 501/111 |
| 6,533,821 B1 | 3/2003 | Lally | |
| 6,835,679 B2 * | 12/2004 | Bilanin et al. | 422/186 |
| 6,939,364 B1 | 9/2005 | Soltz et al. | |
| 7,129,210 B2 | 10/2006 | Lowinger et al. | |
| 2002/0028243 A1 * | 3/2002 | Masters | 424/484 |

OTHER PUBLICATIONS

Merriam-Webster Medical Dictionary (2015), Derive.*
Solorzano, Basic Characteristics of Grancrete HFR (2008), pp. 1-188.*
Azadani et al., Mechanical properties of surgical glues used in aortic root replacement, Ann. Thorac. Surg. (2009), vol. 87, pp. 1154-1160.*
Sanders et al., Mechanical characterization of a bifunctional Tetronic hydrogel adhesive for soft tissues, J. Biomed. Mater. Res. Part A (2015), vol. 103A, pp. 861-868.*
Hermawan, Experimental techniques to determine the Young's modulus of the trachea (2004), pp. 1-109.*
Shirzadi, Biomechanical modeling for lung tumor motion prediction during brachytherapy and radiotherapy, University of Western Ontario—Electronic Thesis and Dissertation Repository (2012), Paper 757, pp. 1-70.*

* cited by examiner

*Primary Examiner* — Abigail Fisher
*Assistant Examiner* — Frank Choi
(74) *Attorney, Agent, or Firm* — Armstrong Teasdale LLP

(57) ABSTRACT

A method for reducing leakage of bodily fluids or air through lung tissue within a patient is provided. In one embodiment, the method comprises applying, to an appropriate area of lung tissue, an adhesive composition that is derived from a mixture of $KH_2PO_4$, metal oxide, a calcium compound, and water, wherein the weight percent ratio of $KH_2PO_4$ and the oxide is at least approximately 1:0.5. The method also comprises polymerizing the adhesive composition to form a sealant that substantially seals the body area with a coating.

17 Claims, 1 Drawing Sheet

METHODS FOR SEALING FLUID LEAKS IN LUNG TISSUE

BACKGROUND OF THE INVENTION

This application relates generally to medical and biological adhesives and more particularly, to methods for bond or sealing living tissues within a patient's lungs using a phosphate-based adhesive.

Conventional methods of closing incisions in soft tissue, such as lung tissue, following surgery and injury, for example, include the use of sutures and/or staples. However, as is known, the use of such surgical methods may be limited. For example, depending on the tissue being repaired, the sutures or stitches may provide an inadequate seal of the tissue resulting in undesirable leakage of fluid or air along the line of joinder. Moreover, such surgical procedures generally require significant surgical skill and may be slow to apply.

To facilitate reducing the likelihood of fluid leakage through a tissue being repaired, at least some surgical methods use a laser to weld or fuse adjoining tissues together. However, the heat necessary to cause the tissue fusion may also cause collateral thermal damage. Moreover, the edges of tissues damaged by the treatment may enable fluid leakage therethrough. As such, because of the risk of transmural and/or collateral thermal injuries, such surgical methods generally require the use of highly-skilled surgeon.

Accordingly, to facilitate the fluid-tight or air-tight sealing of a wound without the issues described above, at least some known surgical procedures use adhesives or glues that are capable of bonding tissue surfaces together rapidly while promoting, or at least not inhibiting, normal healing. For example, at least some known tissue adhesives are fibrin-based and contain a concentrate of fibrinogen and thrombin. Such adhesives are generally two-component adhesives that when mixed together, react to simulate a clot-forming cascade that adheres to tissue and bridges a gap defined between adjoining portions of tissue until healing can occur. However, fibrin-based adhesives may have only limited success because of their low strength and because of the risk of infection associated with the harvesting of fibrin from human blood.

Other known tissue adhesives are based on gelatin being cross-linked with aldehyde, such as gelatin-resorcinol cross-linked with formaldehyde (GRF) or with glutaraldehyde (GRFG). However, the inclusion of aldehyde may cause tissue irritation during use. Moreover, such glues may time-consuming and difficult to use because of the criticality of obtaining the proper cross-linking at the joinder site.

Adhesives found in nature, as well as laser light-induced tissue adhesives have also been used. However, the use of natural product-based adhesives have generally been limited because of the difficulties in purifying appreciable quantities of such materials and the risks associated with triggering an immune response by foreign glycoproteins.

The use of synthetic materials to expedite sealing of tissue is common in the course of surgical procedures concerned with the repair of damaged tissues and vessels. However, generally the adherence of known adhesives used in the repair of tissues in lungs, for example, may be difficult where the tissue surface to be treated may be wet, or covered with blood, mucus, or other secretions. If fluid is present on the surface being repaired, known adhesives may delaminate from the surface after its formation. Moreover, generally known tissue adhesives may lack sufficient mechanical strength (i.e., adhesive properties), may become brittle and/or may not have a sufficient elasticity when formed, and/or may not be biocompatible.

BRIEF SUMMARY OF THE INVENTION

Generally, in one aspect, a method for reducing leakage of bodily fluids or air through lung tissue within a patient is provided. In one embodiment, the method comprises applying, to an appropriate area of lung tissue, an adhesive composition that is derived from a mixture of $KH_2PO_4$, metal oxide, a calcium compound, and water, wherein the weight percent ratio of $KH_2PO_4$, and the oxide is at least approximately 1:0.5. The method also comprises polymerizing the adhesive composition to form a sealant that substantially seals the body area with a coating.

In another aspect, a method of bonding a first lung tissue to a second lung tissue is provided. The method comprises positioning the first lung tissue in proximity to the second lung tissue, and coating at least one of a portion of the first lung tissue and the second lung tissue with an adhesive composition that is derived from a mixture of $KH_2PO_4$, metal oxide, a calcium compound, and water, wherein the weight percent ratio of $KH_2PO_4$ and the oxide is at least approximately 1:0.5.

In a further aspect, a method for sealing an opening in a lung tissue within a patient is provided. The method comprises identifying an area of the tissue having an opening to be sealed, applying to the identified area of lung tissue an adhesive composition that is derived from a mixture of $KH_2PO_4$, metal oxide, a calcium compound, and water, wherein the weight percent ratio of $KH_2PO_4$ and the oxide is at least approximately 1:0.5, and polymerizing the adhesive composition to form a sealant that substantially seals the opening in the lung tissue with a coating that facilitates reducing leakage of bodily fluids or air through the opening.

In yet another aspect, a method for sealing tissue within a patient to facilitate reducing leakage of bodily fluids or air through the tissue is provided. The method comprises identifying an area of the tissue to be sealed, applying to the identified area of tissue an adhesive composition that is derived from a mixture of $KH_2PO_4$, metal oxide, a calcium compound, and water, wherein the weight percent ratio of $KH_2PO_4$ and the oxide is at least approximately 1:0.5, and polymerizing the adhesive composition to form a sealant that substantially seals the identified area with a coating that facilitates reducing leakage of bodily fluids or air through the tissue.

DETAILED DESCRIPTION OF THE INVENTION

Figure 1:
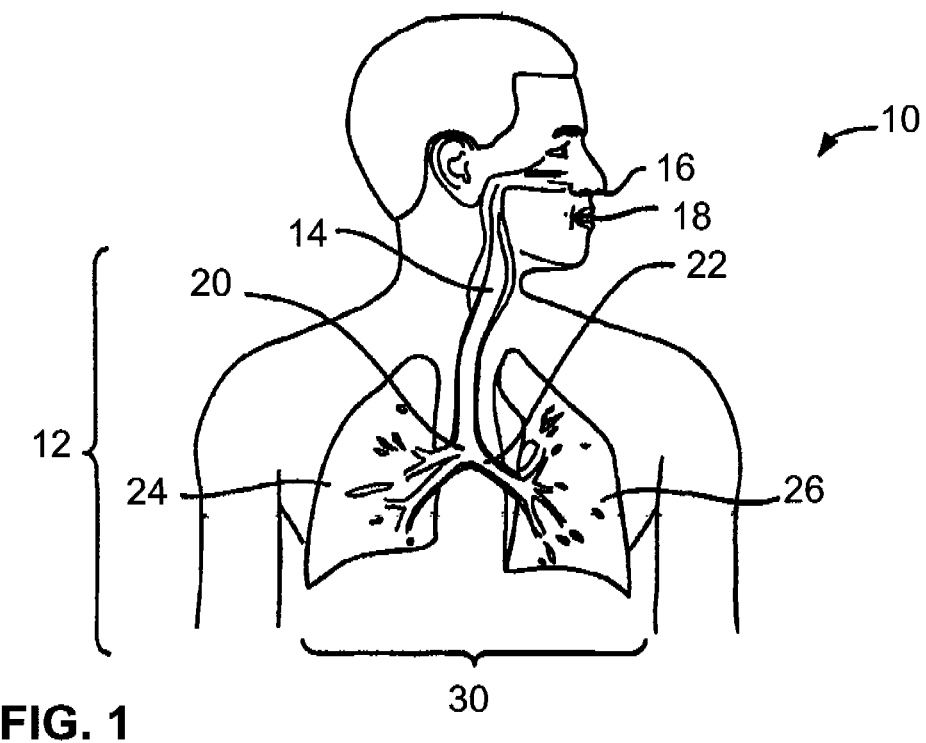
FIG. 1 illustrates an exemplary patient respiratory system 10.

The present invention overcomes the prior art limitations associated with repairing lung tissue and/or sealing fluid leaks in lung tissue. Generally, any surgical procedure for use in repairing a patient's lungs which requires a coating or sealing layer be applied to the patient's lungs, may be treated by the methods described herein with a coating having better adherence and enhanced longevity. For example, lung tissue may be sealed against air leakage after surgery using the techniques described herein. Similarly, lung wounds may be closed, leakage from lung tissues may be stopped or minimized, and/or barriers may be applied to prevent post-surgical adhesions. The methods and adhesives described herein may also be useful in the repair or healing of incisions, abrasions, burns, inflammation, and other conditions requiring application of a coating to the outer surfaces of the patient's lungs.

As used herein, the term "sealant" refers to a material which substantially decreases or prevents the migration of fluid or air from, or into a surface, such as a lung tissue surface. The same materials may also be used to adhere lung tissue materials together, either when applied between adjacent materials, and/or when used to jointly embed the lung tissue materials.

As used herein, the term "biocompatible," refers to a substance which produces no significant untoward or undesirable effects, such as, but not limited to, significant toxicity or adverse immunological reactions, when applied to, or administered to, a patient's lungs, and is distinguished from a mild, transient inflammation which typically accompanies surgery or implantation of foreign objects into a living organism. As used herein the term "biodegradability" refers to the disintegration, which is generally predictable, of a coating into small entities which will be metabolized or excreted, under the conditions normally present in a living tissue.

The term "photosensitizer", as used herein, refers to a compound capable of undergoing photoactivation. Accordingly, photosensitizers can be characterized functionally as those chemicals which absorb electromagnetic energy, such as optical energy, and convert it primarily to chemical energy.

The properties of the particular coating, adhesive, glue, or barrier materials disclosed herein are referred to as "materials properties", and include, but are not limited to only including:

the "Young's modulus of elasticity which is the limiting modulus of elasticity extrapolated to zero strain;

the "elastic modulus" which is any modulus of elasticity, not limited to Young's modulus, and may include other descriptors of non-linear regions of the stress-strain curve; and the "bulk" or "compressive" modulus which is used in its usual sense of ratio of stress to a designated compressive strain;

The term "absorbed" is used herein to encompass both "absorbed" and "adsorbed". Moreover, the term "elastomer," as used herein, refers to a material which at room temperature is capable of repeatedly recovering in size and shape after the removal of a deforming force. In one embodiment, an elastomer is a material which can be repeatedly stretched to at least approximately twice its original length and which will repeatedly return to its approximate length on release of the stress.

Although not intended exclusively for use in tissue sealing, the compositions used with the exemplary methods of the present invention may be referred to as tissue or surgical adhesives, glues, or sealants. All of the foregoing terms are used herein to describe a combination of components capable of adhering, sealing, closing, apposing or otherwise joining, two or more lung tissue elements. The combination of the methods described herein, and the lung tissue glue, also described herein, facilitates the promotion, catalyzation, or otherwise generally causes the formation of covalent bonds between lung tissues, such as, at the edges of a lung wound or surgical incision, so that sealing between lung tissue elements or the formation of a biological lung seal is promoted, as is described herein.

Pulmonary air leakage is a common postoperative complication of respiratory surgery, and prolonged leakage can lead to longer hospitalization, and occasionally even thoracic infections. For example, when lung volume reduction surgery or other lung surgical procedures are performed, a common complication is persistent air leaks which may result in a significant and prolonged air loss from the lung. The incidence of leakage generally increases particularly in procedures on the emphysematous lung. Depending on the location of the defect, and the degree of underlying emphysematous change if any, suturing or stapling can be extremely difficult. Furthermore, sutures may impede re-inflation of the remaining lung. It may also be difficult to suture pulmonary air leakages in the emphysematous lung during thoracoscopy.

In lung surgical procedures in which staples or sutures are utilized, such mechanical fasteners may not effectively prevent air leakage. For example, in lung operations, it is common to make a "wedge resection" to remove diseased areas. Often, as is known, a combination stapler/cutter is used to simultaneously cut and staple along one side of the wedge to be removed, and is then used to staple and cut along the other side of the wedge, such that a wedge-shaped piece of lung tissue may be removed. Moreover, in repairing lacerations within lung tissue, it is also common for staples or sutures to be used. However, in each of the aforementioned procedures, despite the use of a high staple density, staple lines created by the staples may be prone to leak air, which can produce severe complications in a patient undergoing such an operation. Moreover, it is common for leakage to occur through the staple holes which can expand or tear when the lung is re-inflated.

To facilitate overcoming the limitations associated with known procedures for repairing lung tissue and/or sealing fluid leaks in lung tissue, the present invention provides methods that facilitate surgical procedures to be performed to a patient's lungs or to surrounding tissues, while reducing the risks of complications of air leakage through the lung tissue. More specifically, the methods described herein use adhesive compositions that facilitate the glue adhering to lung tissue with low toxicity and such that the glue acts as a sealant to substantially prevent the passage of liquid or gas therethrough. As such, an adhesive connection may be made between biological soft tissues, and/or damage to other tissues may be filled in and/or substantially sealed from a surrounding environment.

Moreover, the present invention provides methods and materials that facilitate diagnostic and therapeutic treatment to a target tissue, such as lung tissue, using a suitable adhesive, such as a glue, as a sealant to prevent the passage of liquid or gas. The materials used in the method include a fast-acting adhesive that cures quickly. In one embodiment, the adhesive sets in less than approximately fifteen minutes. In another embodiment, the adhesive cures in less than one hour. In yet another embodiment, a specific cure time may be tunable to enable glue distribution within the target area before curing fully. In a further embodiment, some glue formulations may require ancillary light sources, such as ultra-violet (UV) light, primers, catalysts, radiofrequency energy, electrical energy or radiation to cause the adhesive composition to cure.

Figure 2:
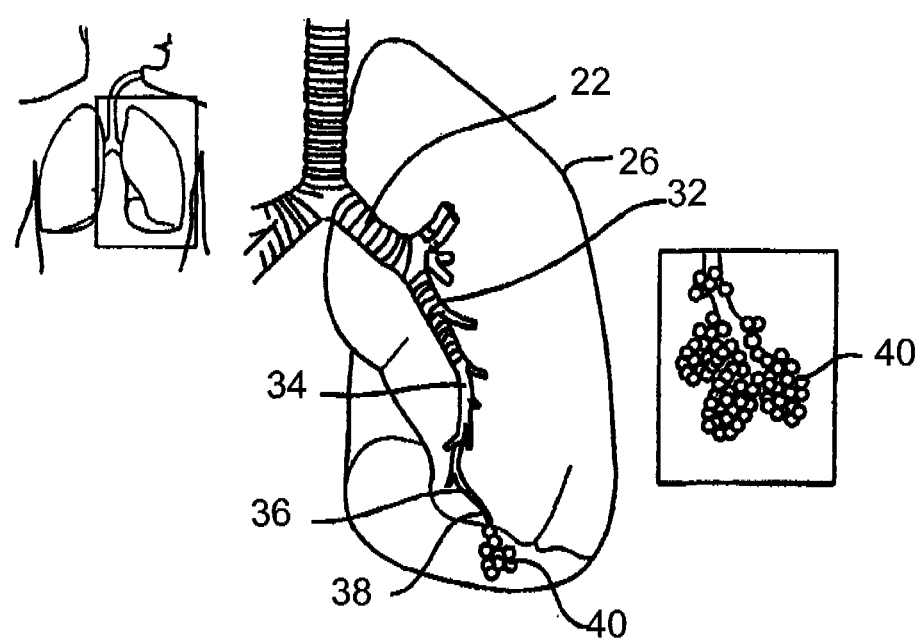
FIG. 2 is an enlarged illustration of a portion of the respiratory system shown in FIG. 1.

FIG. 1 illustrates an exemplary patient respiratory system 10. FIG. 2 is an enlarged illustration of a portion of respiratory system 10. As is known, respiratory system is located primarily within a thoracic cavity 12 and includes the trachea 14, which brings air from the patient's nose 16 or mouth 18 into each of the right and left primary bronchi 20 and 22, respectively. From the right primary bronchus 20 air entering the patient is channeled into the right lung 24, and similarly from the left primary bronchus 22 into the patient's left lung 26. The right lung 24 and the left lung 26, together comprise the patient's lungs 30.

Each primary bronchus 20 and 22 leads into a respective lung 24 and 26 and branches into secondary bronchi 32, and then further into tertiary bronch 34, and still further into bronchioles 36, a terminal bronchiole 38 and finally the alveoli 40. It should be noted that for clarity, only the left lung 26 is illustrated in FIG. 2. A pleural cavity, defined between the lungs 30 and the chest wall, protects the lungs 30 and allows the lungs 30 to move during breathing. More specifically, a thin layer of pleural fluid surrounds the lungs 30 and lubricates the movement of the lungs 30 within thoracic cavity 12.

As such, the lungs 30 are an elastic structure that float within the thoracic cavity 12. The thin layer of pleural fluid that surrounds the lungs 30 lubricates the movement of the lungs 30 within the thoracic cavity 12. Suction of excess fluid from the pleural cavity ensures a slight suction is maintained between the outer surface of the lungs 30 and the inner surface of the thoracic cavity 12. This slight suction also creates a negative pressure that keeps the lungs 30 inflated and floating within the thoracic cavity 12. Without the negative pressure, the lungs 30 collapse like a balloon and expel air through the trachea 14. As such, when the lung tissue is breached, the negative pressure that keeps the lungs 30 in a suspended condition may diminish and the lungs 30 may collapse.

To facilitate substantially sealing lung tissue, in one embodiment, initially an adhesive composition as described in more detail below is applied to at least one surface of the lung tissues to be connected together to form a tissue adhesive combination. The adhesive composition, described in more detail below, facilitates forming a tightly-adherent and compliant, biodegradable sealant that in one embodiment, has material properties substantially similar to those of the lung tissue to which it is applied. More specifically, the adhesive composition forms a structure that is typically stiffer than the intrinsic stiffness of lung tissue and that has a value of the elastic modulus that enables the sealant to expand and contract with the movement of the lungs 30. For example, in one embodiment, the sealant has a value of the elastic modulus of less than about 150.

In each sealing procedure, the amount of the adhesive composition used will, naturally, be dependent on the tissue (s) to which it is being applied and on the size and nature of the wound or incision to be closed or the distance between the tissues to be apposed. The determination of the appropriate amount of the composition to be applied will be known to those of skill in the art in light of the present disclosure.

Moreover, tissue adhesive to seal grafts, fissures, holes, or other openings in lung tissue, the methods of the present invention may also be used to seal conventional closure structures, sutures, staples, and clamps used in lung repair procedures. In such an embodiment, the adhesive composition supplants secondary or tertiary layers of closure structures, or alternatively serves as an added barrier to tissue separation. In addition, the methods and adhesive compositions described herein may be used to adhere lung tissue surfaces to each other. Examples of such applications are tissue grafts and tissue reinforcements or supporting materials, such as meshes used to seal or reconstruct openings, and other tissue-non-tissue interfaces. Adherent coatings can seal the suture lines, support sutured areas against mechanical stress, or substitute entirely for sutures when mechanical stress is low.

The adhesive composition may be applied to the tissue by simply dripping material onto the surface to be coated. For example, such an application may be accomplished using, but is not limited to only using, common devices such as, but not limited to, a syringe, a pipet, or a hose, depending on the amount of composition to be applied and the location of the application. More uniform applications may be obtained using an applicator, such as, but not limited to, a brush, a pad, a sponge, a cloth, or a spreading device such as a finger, a coating blade, a balloon, or a skimming device. In another embodiment, sprayers may be used to apply the adhesive composition. Application techniques may be combined, as in applying fluid from a syringe, and then rubbing it into the surface with a finger tip.

When cured on the lung tissue, the compliance properties of the sealant created are those of the material after it has polymerized to form a flexible, polymerized material. As used herein, the term "polymerized material" includes material which forms by the ionic or covalent reaction of monomer precursor molecules.

The repair methods described herein are advantageous because they can be used to coat and/or to bond together any of a wide variety of surfaces, including, but not limited to, all surfaces of the living body, and surfaces of medical devices, implants, wound dressings and other body-contacting artificial or natural surfaces. For example, the adhesive component may be applicable to diagnostic and therapeutic procedures, including but not limited to, treatment modalities, and devices suitable for use elsewhere in a patient, such as, but not limited to, liver tissues, connective tissues, pancreatic tissue, breast tissue, kidney tissue, gastrointestinal tract tissues, and/or prostate tissue. Moreover, the repair methods described herein may be used with at least one surface selected from the following: a surface of the respiratory tract, the meninges, the synovial spaces of the body, the peritoneum, the pericardium, the synovia of the tendons and joints, the renal capsule and other serosae, the dermis and epidermis, the site of an anastomosis, a suture, a staple, a puncture, an incision, a laceration, or an apposition of tissue, a ureter or urethra, a bowel, and/or the esophagus. Treatment modalities include, but are not limited to, filling voids, repairing tissue lacerations, and repairing dissections.

In other embodiments, the present invention may be used in conjunction with cardiovascular surgery, including, but not limited to, for use as a tissue sealant to stop bleeding from a vascular suture line, support of vascular graft attachment, enhancing pre-clotting of porous vascular grafts, stanching of diffuse nonspecific bleeding, anastomoses of cardiac arteries, especially in bypass surgery; support of heart valve replacement; sealing of patches to correct septal defects, bleeding after sternotomy, and/or arterial plugging.

In each embodiment, in the particular application area of coating of tissues, cells, medical devices, and capsules, formation of implants for drug delivery or as mechanical barriers or supports, and other biologically related uses, the adhesive composition is biocompatible and lacks toxicity. Moreover, because the sealant created is biodegradable, it does not have to be retrieved from the body.

In another embodiment, sealing may be facilitated with the use of a patch. A "patch" is defined herein to include any shaped substrate compatible with surgical implantation and capable of being coated by the adhesive composition using the methods of the present invention. Patches may be of any shape, and may be fabricated from any material that facilitates sealing including, but not limited to, collagen; polylactic acid; hyaluronic acid; fluoropolymers; silicones; knitted or woven meshes of, for example, cellulosic fibers, polyamides, rayon acetates and titanium; skin; bone; titanium and stainless steel. For example, a tissue adhesive patch can be used to bond tissues together, rather than overlapping adjacent layers of tissues. In each embodiment, the patch is biologically compatible and non-irritating.

The adhesive composition facilitates forming a tightly-adherent and compliant, biodegradable sealant that in one embodiment, has material properties substantially similar to those of the lung tissue to which it is applied. Moreover, in one embodiment, the feature of the invention is that the adhesive "sets" at physiologic temperatures and pH, in less than approximately fifteen minutes. In addition, the bio-adhesive composition is an elastomer that expands in vivo such that it may be used to simultaneously fill lung tissue voids while providing structural support. Another advantage is that the expandability of the adhesive during setting or curing confers additional mechanical contact between the adhesive and adjacent tissue layers being bonded together and/or between a tissue layer and an adjacent structure being bonded to the tissue layer.

In each embodiment, the adhesive composition is gradually absorbed by the body without rejection. The adhesive composition facilitates the repair of lung tissue at a myriad of temperatures, pH ranges, humidity levels and pressures. The mixture typically is injectable, prior to setting, and exhibits neutral pH after setting.

Generally, the bio-adhesive is derived from a hydrated mixture which comprises $KH_2PO_4$, a metal oxide, and a calcium containing compound. A preferred mixture is the following: $KH_2PO_4$ 45 percent, MgO 45 percent, Calcium-containing compound 10 percent (whereby compound is either $CaSiO_3$ or $Ca_{10}(PO_4)_6(OH)_2$), and $H_2O$ 25 percent by weight. Alternatively, a range of the constituents can be utilized. For example, between 40 and 50 percent by weight of the $KH_2PO_4$ can be utilized, and/or between 35 and 50 percent by weight of the MgO also can be utilized. In one embodiment, the ratio of $KH_2PO_4$ to MgO is between about 1:0.5 and 1:1. In addition, aside from MgO, a myriad of other oxide and hydroxide powders can be utilized, including, but not limited to FeO, $Al(OH)_3$, $Fe_2O_3$, $F_3O_4$ and $Zr(OH)_4$. During use, the magnesium oxide reacts with water and/or serum in and around the living tissue to yield $Mg(OH)_2$ and magnesium salts. In one embodiment, the cured material is an elastomer that expands to between about 0.15 and 0.20 percent of volume.

In the exemplary embodiment, oxide powder is a salient ingredient in the mixture. Optionally, the oxide is subjected to a calcination process. Calcination durations and temperatures are determined empirically, depending on the final characteristics and setting times desired. Generally, however, calcination temperatures of up to about 1300° C. for up to several hours are typical. Generally, pharmaceutical grade oxides are utilized.

After calcination, the oxide powder is mixed with the potassium phosphate compound and the compound tricalcium phosphate until a substantially homogenous dry-phase results. One method for sizing and homogenizing the various powders is via vibratory milling. Another homogenization method utilizes a ribbon mixer wherein the particles are ground to a fineness of approximately 20-30 microns. Upon homogenization, wherein all of the constituents are contained in a dry homogenous mixture, water is added up to 25 percent of the weight of the resulting slurry.

Bonding occurs primarily between the tissue and adjacent tissue and/or structure. Notably, the adhesive composition also bonds to itself. In one embodiment, the use of phosphoric acid, rather than water, facilitates increasing the bonding strength of the resulting material. The molarity of the phosphoric acid can vary, as long as the eventual pH of the slurry is not hazardous to the patient, or contraindicative to healing. Generally, a slurry pH of between about six to about eight is appropriate.

The inorganic bio-adhesive has been found to be non-toxic to cells and absorbable in situ. It rapidly attains strengths of more than 9000 pounds per square inch (psi). The adhesive composition sets in water, so as to be a suitable water hydraulic cement, and can be instantly cured (i.e., hardened) by an outside heat source, such as, but not limited to, ultraviolet light.

Exemplary formulations of the adhesive binder include the following:

Magnesium potassium phosphate (technical grade-30 microns) 64%*, Magnesium oxide (technical grade) 32%, Tricalcium Phosphate 32% *Weight percent;

Magnesium potassium phosphate (technical grade as above) 61%*, Magnesium oxide (technical grade-calcined) 31%, Tricalcium phosphate 4%, $CaSiO_3$ 4% *Weight percent;

Magnesium potassium phosphate 45%*, Magnesium oxide 45%, Tricalcium phosphate 10% *Weight percent:

Magnesium potassium phosphate 41%* Magnesium oxide 41%, Tricalcium phosphate 9%, Calcium silicate 9% *Weight percent Water is added to up to 25 weight percent of the formulation, and preferably about 22 to 25 weight percent; and/or Magnesium potassium phosphate 41%*, Magnesium oxide 41%, Tricalcium phosphate 9%, Silicon dioxide 9%*Weight Percent Water is added up to about 25 weight percent and preferably between about 22 and 25 weight percent.

The amount of water added depends on the workability desired. Generally, and unless additional heat is applied, the exothermic reaction resulting from the slurry formation results in the full curing in approximately three hours or less. The new refractory results in a final green strength of approximately 8500 psi. In one embodiment, a photosensitizer ingredient is added to the adhesive composition. In another embodiment, an external heat source, i.e., a UV light, facilitates curing the adhesive composition within minutes. In such an embodiment, a localized light source such as a fiber optic or light guide, which can project radiation of the appropriate wavelength onto the site to be treated to cause polymerization of the adhesive composition. In another embodiment, electromagnetic radiation is applied to the adhesive composition to promote the formation of an adhesive connection between the tissues. In another embodiment, the adhesive composition may be used to channel a pharmaceutical composition to the lung tissue.

A variety of materials are suitable for addition to the adhesive composition. In general, the materials are inert so that they do not readily react with the biologically compatible sealant under physiological buffer conditions and/or body temperatures. Non-limiting examples of such materials include glass, semi-conductors such as silicon and germanium, metals such as platinum and gold, and a vast number of plastic polymers, such as polyamide (PA), polyimide (PI), polyacrylonitrile (PAN), polybutylene (PB), polybutadiene (PBD), polycaprolactam (PCL), polyethylene (PE), polychlorotrifluoroethylene (PCTFE), polytetrafluoroethylene (PTFE), polydimethylsiloxane (PDMS), polyethylene terephathalate (PET), polyisobutylene (PIB), polystyrene (PS), polyolefine (PO), polymeric polyisocyanate (PPI), polyvinylchloride (PVC), polyvinylidene chloride (PVDC), polyvinyl fluoride (PVF), acrylonitrile-acryloid-styrene (AAS), acrylonitrile-butadiene-styrene (ABS), acrylonitrile-chlorizate ethylene-styrene (ACS), and any other inert polymers provided by commercial vendors. Many of the aforementioned material additives faciltiate tissue binding to form localized adhesions or a bio-response that will help maintain permanent pleurae bonding of the lung tissue.

Adhesive formulations for use with the above-described methods may include, but are not limited to only including, solids, semi-solids, hydrogels, foams, agars or sol-gels. Some glue formulations work in wet or dry tissue surface conditions. Some glue formulations may also stop active bleeding (i.e., provide hemostasis). The adhesive formulations are flexible and conformable to tissue geometry, and they possess high tensile strength. Optionally, a foaming agent may be added to the adhesive composition.

In one embodiment, the glue formulation crosslinks (chemically bonds) to the biological tissue it is applied to. More specifically, the adhesive either crosslinks to collagen or promotes the crosslinking of collagen at two adjoining lung tissue surfaces to be fused and allow for high adhesion. In another embodiment, the glue formulation includes a radiopaque component so that the glued boundary can be identified using x-ray-based imaging techniques during or after the procedure. Such additives may include, but are not limited to only including, tantalum, platinum, bismuth, radiopaque metals and polymers. Polymers can include, for example, poly(lactic acid) and poly(glycolide).

Generally, the sealant will cure within a few minutes, works well in a damp or wet environment, and blocks air or fluid from entering the pleural cavity. The present invention overcomes the problems associated with fibrinogen, as well as the risk of transmission of viral infections inherent in the use of pooled donor blood. The present invention also overcomes the problem of the time involved in surgical lung repair procedures. The present invention overcomes these and other drawbacks in the prior art by providing lung tissue repair methods which use adhesive compositions that facilitate lung tissue sealing and wound healing without requiring the use of heat. The lack of heat facilitates an effective seal with minimal tissue distortion or damage to surrounding collateral areas.

The above-described lung tissue repair and sealing methods are cost-effective and highly reliable. The repair methods use an adhesive composition that forms a sealant that enables lung wounds to be closed, leakage from lung tissues to be substantially stopped or minimized, and barriers to be applied to prevent post-surgical adhesions. Moreover, the above-described repair methods enable lung tissue to be repaired in a non-invasive manner that does not require the use of mechanical hardware. The sealant formed is biodegradable, flexible, and is resilient to fluids. As a result, lung tissue may be repaired in a cost-effective and highly reliable manner.

Exemplary embodiments of lung repair techniques and adhesive compositions are described above in detail. The techniques and adhesive compositions are not limited to use with the specific embodiments described herein, but rather, components of each repair procedure, and/or adhesive composition, can be utilized independently and separately from other carton repair procedures and/or adhesive compositions described herein. Moreover, the invention is not limited to only being used with lungs. Rather, other bodily tissues may be sealed within the spirit and scope of the claims.

While the invention has been described in terms of various specific embodiments, those skilled in the art will recognize that the invention can be practiced with modification within the spirit and scope of the claims.

What is claimed is:

1. A method for reducing leakage of bodily fluids or air through lung tissue within a patient, said method comprising:
    applying, to an appropriate area of lung tissue, an adhesive composition that comprises a mixture of KH2PO4, metal oxide, a calcium compound, an elastomer, and water, wherein the weight percent ratio of KH2PO4 and the oxide is at least approximately 1:0.5; and
    curing the adhesive composition to form a seal which is effective to reduce leakage of bodily fluids or air through said lung tissue.

2. A method in accordance with claim 1 wherein applying, to an appropriate area of lung tissue, further comprises applying an adhesive composition wherein the weight percent ratio of KH2PO4 and the oxide is between approximately 1:0.5 and 1:1.

3. A method in accordance with claim 1 wherein applying, to an appropriate area of lung tissue, further comprises applying a biodegradable adhesive composition to the appropriate area of lung tissue.

4. A method in accordance with claim 1 wherein applying, to an appropriate area of lung tissue, further comprises:
    applying the adhesive composition to at least one of a tissue graft and the appropriate area of lung tissue; and
    positioning the graft against the appropriate area of lung tissue such that the adhesive composition effectively reduces leakage of bodily fluids or air between the outer edges of said graft and said lung tissue.

5. A method in accordance with claim 1 wherein curing the adhesive composition further comprises using an ultraviolet light to facilitate curing of the adhesive composition.

6. A method in accordance with claim 1 wherein curing the adhesive composition further comprises using electromagnetic radiation to facilitate curing of the adhesive composition.

7. A method of bonding a first lung tissue to a second lung tissue, said method comprising:
    positioning the first lung tissue in proximity to the second lung tissue;
    coating at least one of a portion of the first lung tissue and the second lung tissue with an adhesive composition that comprises a mixture of KH2PO4, metal oxide, a calcium compound, an elastomer, and water, wherein the weight percent ratio of KH2PO4 and the oxide is at least approximately 1:0.5; and
    bonding the first lung tissue to the second lung tissue.

8. A method in accordance with claim 7 further comprising curing the adhesive composition to form a sealant.

9. A method in accordance with claim 7 wherein coating at least one of a portion of the first lung tissue and the second lung tissue further comprises applying an adhesive composition to one of the first and second lung tissues, wherein the weight percent ratio of KH2PO4 and the oxide is between approximately 1:0.5 and 1:1.

10. A method in accordance with claim 7 wherein coating at least one of a portion of the first lung tissue and the second lung tissue further comprises
    applying a biodegradable adhesive composition to one of the first and second lung tissues.

11. A method in accordance with claim 7 wherein coating at least one of a portion of the first lung tissue and the second lung tissue further comprises:

applying the adhesive composition to at least one of a tissue graft and a patch; and positioning the at least one of the tissue graft and the patch against at least one of the first lung tissue and the second lung tissue, such that the adhesive composition effectively bonds the outer edges of at least one of the tissue graft and the patch to the lung tissue.

12. A method in accordance with claim 7 further comprising curing the adhesive composition using an ultraviolet light.

13. A method in accordance with claim 7 further comprising curing the adhesive composition using electromagnetic radiation.

14. A method for sealing lung tissue within a patient to facilitate reducing leakage of bodily fluids or air through the lung tissue, said method comprising:

identifying an area of the lung tissue to be sealed;

applying to the identified area of lung tissue an adhesive composition that comprises a mixture of KH2PO4, metal oxide, a calcium compound, an elastomer, and water, wherein the weight percent ratio of KH2PO4 and the oxide is at least approximately 1:0.5; and curing the adhesive composition to coat the identified area with a seal that is effective to facilitate reducing leakage of bodily fluids or air through the lung tissue.

15. A method in accordance with claim 14 wherein curing the adhesive composition further comprises using at least one of an ultraviolet light and an electromagnetic radiation to facilitate curing of the adhesive composition.

16. A method in accordance with claim 14 wherein applying to the identified area of lung tissue an adhesive composition further comprises applying an adhesive composition wherein the weight percent ratio of KH2PO4 and the oxide is between approximately 1:0.5 and 1:1.

17. A method for sealing an opening in a lung tissue within a patient, said method comprising:

identifying an area of the tissue having an opening to be sealed;

applying to the identified area of lung tissue an adhesive composition that comprises a mixture of KH2PO4, metal oxide, a calcium compound, an elastomer, and water, wherein the weight percent ratio of KH2PO4 and the oxide is at least approximately 1:0.5; and curing the adhesive composition to seal the opening in the lung tissue with a coating that is effective to reduce leakage of bodily fluids or air through the opening.

* * * * *